United States Patent [19]

Kramer

[11] 4,335,253
[45] Jun. 15, 1982

[54] PREPARATION OF DIHALOVINYL COMPOUNDS

[75] Inventor: Petrus A. Kramer, Amsterdam, Netherlands

[73] Assignee: Shell Oil Company, Houston, Tex.

[21] Appl. No.: 266,578

[22] Filed: May 22, 1981

[30] Foreign Application Priority Data

May 30, 1980 [GB] United Kingdom ................. 8017697

[51] Int. Cl.$^3$ .................... C07C 67/317; C07C 45/65; C07C 41/48
[52] U.S. Cl. .................................. 560/124; 568/346; 568/591; 568/347; 570/217
[58] Field of Search ................ 560/124; 570/216, 218, 570/217; 568/347, 591, 346

[56] References Cited

U.S. PATENT DOCUMENTS 4,018,838 4/1977 Cleare .............................. 260/654 R
4,166,063 8/1979 Martel et al. ................. 260/343.3 R Primary Examiner—Michael Shippen

[57] ABSTRACT

A process for the preparation of dihalovinyl compounds of the formula

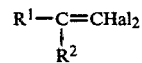

wherein each Hal is fluorine, chlorine or bromine, $R^1$ is an optionally substituted hydrocarbyl group, $R^2$ is a methyl group or a hydrogen atom, or $R^1$ and $R^2$ together with the carbon atom to which they are attached form cycloalkylidene group, which process comprises treating a trihalo compound of the formula

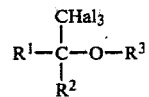

wherein Hal, $R^1$ and $R^2$ have the above meanings and $R^3$ is a hydrogen atom or

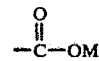

in which M is an alkali atom, with $PHal_3$.

9 Claims, No Drawings

PREPARATION OF DIHALOVINYL COMPOUNDS

BACKGROUND OF THE INVENTION

1. Field of the Invention

The present invention is directed to a process for the preparation of dihalovinyl compounds.

2. Description of the Prior Art 2-(2,2-Dihalovinyl)-3,3-dimethylcyclopropyl compounds and 1,1-dihaloalkene compounds are known intermediates in the preparation of known cyclopropanecarboxylate pyrethroid esters of U.S. Pat. No. 4,024,163.

These pyrethroids show remarkable activities against various insects. Moreover these compounds show very low mammalian toxicity which makes them extremely useful as pesticides for crop protection. Thus bollworm species which infest cotton and cotton leaf worms which are leaf-eating pests are effectively combatted with pyrethroids. Pyrethroids have shown their usefulness as pesticides for fruit and vegetable protection.

Also for animal health protection pyrethroids can successfully be applied. For example against red mites which are found in the cracks and crevices of poultry houses, particularly on perches, and which cause loss of condition by feeding on the blood of the birds. Another application of pyrethroids is against some kinds of beetles which may cause serious structural damage to buildings especially those containing wood or polystyrene. The proved usefulness of pyrethroids stimulates Research and Development to find novel intermediates and novel economic routes to pyrethroids. It is the object of the present invention to provide a process for preparation of useful 2,2-dihalovinyl compounds.

From U.S. Pat. No. 4,018,838 a process for the preparation of dihalo-substituted alkene pyrethroid intermediates is known. The process comprises the reductive dehydrohalogenation of alpha-haloalcohols to give dihalo-substituted alkenes using zinc dust and acetic acid.

The present process obviates the use of zinc and acetic acid in the preparation of the dihalovinyl compounds which make this process not only novel but also economically and technically attractive.

SUMMARY OF THE INVENTION

Accordingly the present invention provides a process for the preparation of dihalovinyl compounds of general formula:

wherein $R^1$ represents an optionally substituted hydrocarbyl group, $R^2$ a methyl group or a hydrogen atom, or $R^1$ and $R^2$, together with the carbon atom to which they are attached, form a cycloalkylidene group having 3 to 6 carbon atoms, and each Hal is selected from fluorine, chlorine and bromine. The process comprises the reaction of the trihalo compound of the general formula:

wherein $R^1$ and $R^2$ have the same meaning as in formula I, at least one Hal is bromine, the other Hal's having the same meaning as in formula I, and $R^3$ is hydrogen or

wherein M is an alkali metal atom, with $PHal_3$, wherein Hal is selected from bromine and chlorine.

The alkali metal atom represented by M is preferably sodium or potassium. Preferred trihalo compounds of formula II are those in which $R^1$ represents an optionally 2'-substituted-3,3-dimethyl cyclopropyl group, because such compounds are preferred intermediates in the preparation of pyrethroids. Among these compounds those in which $R^1$ represents a 2'-alkoxycarbonyl-3',3'-dimethyl cyclopropyl group, in which the alkoxy group has from one to ten carbon atoms, are preferred. Alkoxy groups having 1-3 carbon atoms are particularly preferred. This alkoxy group is preferably a methoxy or an ethoxy group; methoxy groups are most preferred. Other examples of 2'-substituted-3',3'-dimethyl cyclopropyl groups include a 2'-(2,2-dimethoxyethyl)-3',3'-dimethylcyclopropyl group or a 2'-(2-oxopropyl)-3',3'-dimethylcyclopropylmethyl group.

The present process may also be carried out with trihalo compounds of formula II in which $R^1$ represents an optionally substituted alkyl group with fewer than ten carbon atoms. Examples of such alkyl groups are isopropyl, ethyl and methyl groups.

The process is suitably carried out at a temperature in the range of from about 0° to about 200° C. Temperatures in the range of from about 40° to about 160° C. are preferred.

The reaction of the trihalo compound II with phosphorus halide is preferably carried out in the presence of a polar, aprotic solvent. The term "aprotic" as used herein denotes a solvent which is free from hydrogen atoms that are able to form hydrogen bond with anions. These definitions are in accordance with "Physical Chemistry of Organic Solvent Systems", edited by A. K. Corrington and T. Kickinson, Plenum Press (1973), pages 332 and 333.

Preferred polar, aprotic solvents include N,N-dimethylformamide, N,N-dimethylacetamide, and N-methyl-2-pyrrolidone. Solvent mixtures of e.g. toluene, cyclohexane and one or more of the above polar aprotic solvents may also be used. Dimethylformamide is preferred.

The molar ratio of the reactants, i.e. the trihalo compound II and $PHal_3$ is suitably in the range of from about 1:10 to about 1:1. Preferably the range is of from about 1:2 to about 1:1.1.

The starting materials for the present process can be prepared, for example, as described in U.S. Pat. Nos. 4,018,838 and 4,166,063 and copending U.S. Pat. Nos. 4,285,882, 4,307,243 and 4,281,203 as well as Japanese patent applications Nos. 52/73,842 and 52/73,843, each published June 21, 1977, and European patent application No. 80/200,240.

The starting materials and products often may exist as geometric and/or optical isomers because of the unsaturation or e.g. the cyclopropane ring. The cis or trans optical configuration in the cyclopropyl ring containing substituent is usually preferred because the resulting pyrethroid esters usually have a higher pesticidal activity than the cis/trans mixtures. This process is applicable to both cis and/or trans forms.

EXAMPLES

The invention is further illustrated by the following examples which describe the preparation of typical species of the invention. These examples are provided for the purpose of illustration only and should not be regarded as limiting the invention in any way.

The following examples further illustrate the invention. The term "selectivity" used in the examples has the following meaning. The selectivity to a certain component expressed in a percentage, is defined as (a/b)×100, wherein "a" is the amount of the starting compound converted into that certain compound and "b" is the amount of converted starting compound.

Example I

Preparation of ethyl trans 2'-(2,2-dibromovinyl)3',3'-dimethyl cyclopropane carboxylate (compound 1)

An NMR tube was charged with a solution of 40 mg (0.095 mmol) ethyl trans 2'-(2,2,2-tribromo-1-hydroxyethyl)-3',3' dimethyl cyclopropane carboxylate (compound 2) and 14.5 mg (0.105 mmol) phosphorustrichloride in 0.5 ml N,N-dimethylformamide (DMF). After heating for 35 minutes at 50° C. the reaction mixture was diluted with 1 ml water and extracted with 0.5 ml CDCl$_3$. The CDCl$_3$ layer was washed three times with 1 ml water, dried over MgSO$_4$ and analysed by NMR GLC. Conversion 100%, selectivity 93% ethyl trans 2'-(2,2-dibromovinyl)-3',3'-dimethyl cyclopropane carboxylate.

Example II

Preparation of methyl cis 2'-(2,2-dibromovinyl)3',3' dimethyl cyclopropane carboxylate (compound 3)

The above compound was prepared in a one-pot procedure in which at first sodium 2,2,2-tribromo-1-(3',3'-dimethyl-2'-methoxycarbonyl cyclopropyl) ethyl carbonate was prepared by adding 1.5 g cis methylcaronaldate (9.6 mmol) (compound 4) during five minutes at 5° C. to a suspension of 4 g sodiumtribromoacetate (12.5 mmol) in 15 ml DMF (DMF was dried over mol.-sieves). And after stirring for 50 min at 5° C. 1.1 ml PCl$_3$ (12.5 mmol) was added during 2 min while cooling (exothermic reaction, temp. ≦15° C.). Subsequently the reaction mixture was heated during 30 min at 80° C. and quenched in 75 ml water after cooling to room temperature. Afterwards the organic phase was extracted with pentane (3×15 ml) and the collected pentane extracts were combined and washed with water (2×20 ml) and a saturated NaHCO$_3$ solution (2×20 ml), dried over anhydrous MgSO$_4$, filtered and the solvent was removed under reduced pressure leaving a yellow oil (3.2 g) of which the content of methyl cis 2'-(2,2-dibromovinyl)-3',3'-dimethyl cyclopropane carboxylate was more than 90%. The conversion of the starting methyl ester was more than 95% with a selectivity to the dibromovinyl compound of more than 95%.

Example III

Preparation of methyl cis 2'-(2-bromo-2-chlorovinyl)-3',3'-dimethyl cyclopropane carboxylate (compound 5)

106 mg PCl$_3$ (0.77 mmol) was added to a solution of 160 mg (0.44 mmol) methyl cis 2-(2,2 dibromo-2-chloro-1-hydroxyethyl)-3,3-dimethyl cyclopropane carboxylate (compound 6) in 0.5 ml DMF and the mixture was heated during 30 min at 60° C. Working up in the usual way afforded methyl cis 2'-(2-bromo2-chlorovinyl)-3',3'-dimethyl cyclopropane carboxylate. Conversion and selectivity were more than 95%.

Example IV

Preparation of ethyl trans 2'-(2,2-dibromovinyl)3',3'-dimethyl cyclopropane carboxylate (compound 1)

0.12 mmol (50 mg) ethyl trans 2'-(2,2,2-tribromo-1-hydroxyethyl)-3',3'-dimethyl cyclopropane carboxylate (compound 2) and 0.13 mmol (35 mg) phosphorus tribromide were heated during 30 minutes at 50° C. in 0.5 ml DMF. Ethyl trans 2'-(2,2 dibromovinyl)-3',3'-dimethyl cyclopropane carboxylate was obtained in more than 95% yield. Conversion 100%, selectivity more than 95%.

Example V

Preparation of n 1,1-dibromooctene-1

71.3 mg 1,1,1-tribromo-2-hydroxyoctane (0.20 mmol) and 30.2 mg PCl$_3$ (0.22 mmol) in 0.5 ml DMF were heated during 50 minutes at 140° C. After cooling to 20° C. and dilution with 1 ml water, the organic phase was extracted with 0.5 ml CDCl$_3$ and the CDCl$_3$ extract was washed with water (3×1 ml). NMR and GLC analyses showed: conversion 95%, selectivity 83%.

Example VI

A comparative experiment was carried out by the preparation of ethyl trans 2'-(2,2 dibromovinyl)-3',3'-dimethyl cyclopropane carboxylate (compound 1) by reacting the trihalo compound with zinc/acetic acid.

0.35 Mmol (23 mg) Zn was added to a stirred solution of 0.24 mmol (100 mg) ethyl trans 2'-(2,2,2-tribromo-1-hydroxyethyl)-3',3'-dimethyl cyclopropane carboxylate (compound 2) in 230 μl acetic acid at 50° C. After 40 minutes the clear solution was diluted with 10 ml water and extracted with pentane (3×5 ml). The collected pentane extracts were washed with water (3×5 ml), dried over MgSO$_4$, filtered and the solvent was removed under reduced pressure leaving 52 mg of an oil. Conversion 85%, selectivity to dibromovinylester 21% (NMR and GLC analyses), the rest being overreduced compounds.

Conversion and selectivity of the above reaction using zinc/acetic acid appears to be much lower than those of the reactions according to the present invention.

I claim:

1. A process for the preparation of a 2,2-dihalovinyl compound of the formula:

wherein R¹ represents a 2'-(2,2-dimethoxyethyl)-3',3'-dimethylcyclopropyl group, a 2'-(2-oxopropyl)-3',3'-dimethylcyclopropyl group or a 2'-(alkoxycarbonyl)-3,3-dimethylcyclopropyl group in which the alkoxy group contains from 1 to 10 carbon atoms; R² represents a hydrogen atom; and each Hal is selected from fluorine, chlorine or bromine, which process comprises reacting a trihalo compound of the formula:

 (II)

wherein R¹ and R² have the same meaning as in formula I, at least one Hal is bromine, the other Hal's having the same meaning as in formula I, and R³ is hydrogen, or

C—OM, wherein M is an alkali metal atom, with PHal₃, wherein Hal is selected from bromide and chlorine.

2. A process according to claim 1 characterized in that M is sodium.

3. A process according to claim 1, characterized in that R¹ represents a 2'-alkoxycarbonyl-3',3'-dimethyl cyclopropyl group in which the alkoxy group has from one to ten carbon atoms.

4. A process according to claim 3, characterized in that the alkoxy group has 1-3 carbon atoms.

5. A process according to claim 4, characterized in that R¹ represents a 2'-methoxycarbonyl-3',3'-dimethyl cyclopropyl group.

6. A process according to claim 1, characterized in that it is carried out at a temperature in the range of from about 40° C. to about 160° C.

7. A process according to claim 1, characterized in that the reaction of the trihalo compound II with the phosphorus halide is carried out in the presence of a polar, aprotic solvent.

8. A process according to claim 7, characterized in that the polar, aprotic solvent is selected from N,N-dimethylformamide, N,N-dimethylacetamide and N-methyl-2-pyrrolidone.

9. A process according to claim 1, characterized in that the molar ratio of the trihalo compound (II) and PHal₃ is in the range of from about 1:2 to about 1:1.1.

* * * * *